United States Patent
Chaar et al.

(10) Patent No.: US 10,524,891 B1
(45) Date of Patent: Jan. 7, 2020

(54) INFERIOR VENA CAVA FILTER RETRIEVAL DEVICE AND METHOD OF RETRIEVING SAME

(71) Applicant: Yale University, New Haven, CT (US)

(72) Inventors: Cassius Iyad ochoa Chaar, New Haven, CT (US); Daniel Rodion Rathbone, New Haven, CT (US); Joseph Zinter, New Haven, CT (US)

(73) Assignee: Yale University, New Haven, CT (US)

( * ) Notice: Subject to any disclaimer, the term of this patent is extended or adjusted under 35 U.S.C. 154(b) by 566 days.

(21) Appl. No.: 14/844,775

(22) Filed: Sep. 3, 2015

Related U.S. Application Data

(60) Provisional application No. 62/046,413, filed on Sep. 5, 2014.

(51) Int. Cl.
*A61F 2/01* (2006.01)

(52) U.S. Cl.
CPC .......... *A61F 2/01* (2013.01); *A61F 2002/011* (2013.01)

(58) Field of Classification Search
CPC ........ A61F 2/01; A61F 2002/011; A61F 2/95; A61F 2/2427; A61F 2002/9528; A61F 2002/9534; A61B 2017/22035; A61M 25/0105; A61M 25/0133; A61M 25/0147
See application file for complete search history.

(56) References Cited

U.S. PATENT DOCUMENTS

| | | | |
|---|---|---|---|
| 4,926,858 A * | 5/1990 | Gifford, III | A61B 17/22031 604/22 |
| 6,187,016 B1 * | 2/2001 | Hedges | A61B 17/221 606/108 |
| 6,726,621 B2 | 4/2004 | Suon et al. | |
| 2002/0045918 A1 | 4/2002 | Suon et al. | |
| 2002/0120277 A1 * | 8/2002 | Hauschild | A61B 17/221 606/108 |
| 2007/0186933 A1 * | 8/2007 | Domingo | A61B 17/12022 128/207.15 |
| 2008/0281293 A1 * | 11/2008 | Peh | A61B 1/00082 604/523 |
| 2014/0012368 A1 | 1/2014 | Sugimoto et al. | |
| 2014/0031854 A1 | 1/2014 | Goode et al. | |
| 2014/0074109 A1 * | 3/2014 | Resnick | A61B 17/50 606/113 |

* cited by examiner

*Primary Examiner* — Katherine M Rodjom
(74) *Attorney, Agent, or Firm* — Carmody Torrance Sandak & Hennessey LLP

(57) ABSTRACT

A medical device for retrieving an inferior vena cava filter from an inferior vena cava having a handle having a distal end, wherein a longitudinal axis is defined thereby; a grasping assembly coupled to the handle, wherein the grasping assembly comprises a grasper for grasping the inferior vena cava filter positioned within the inferior vena cava, and an articulation assembly coupled to the grasping assembly for causing the grasping assembly to move laterally with respect to the longitudinal axis of the handle. Methods of retrieving an inferior vena cava filter from an inferior vena cava are also disclosed.

9 Claims, 13 Drawing Sheets

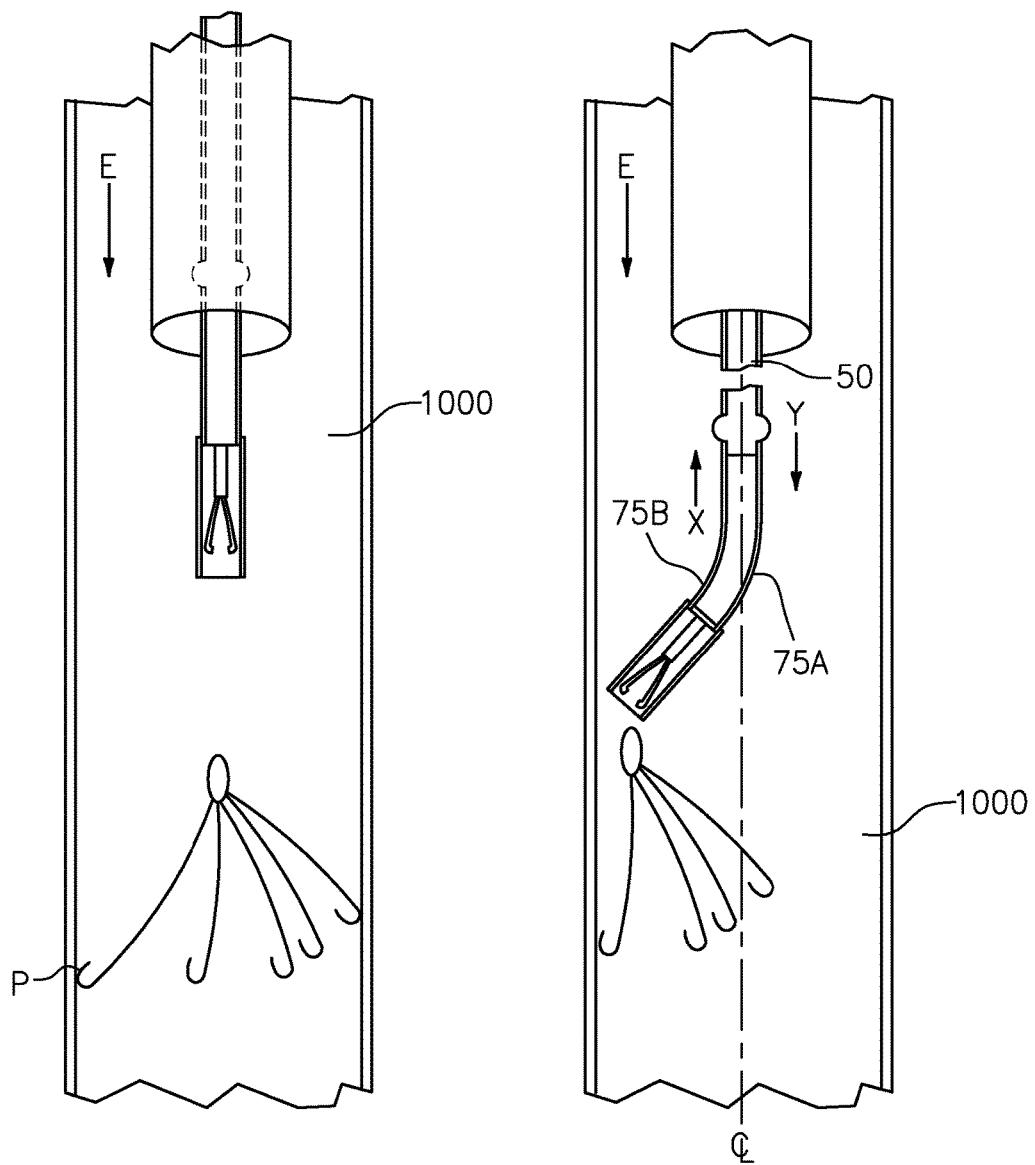
*FIG. 6A*   *FIG. 6B*

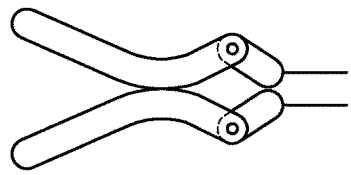
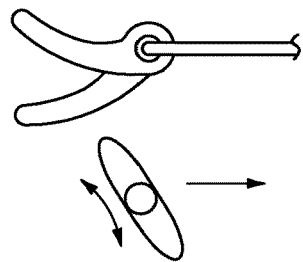
FIG. 9A  FIG. 9B
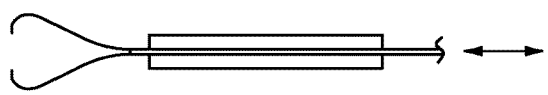
FIG. 9C
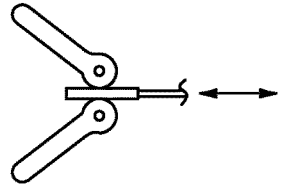
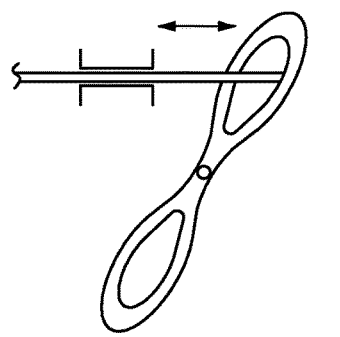
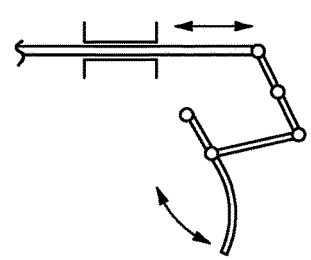
FIG. 9D  FIG. 9E  FIG. 9F
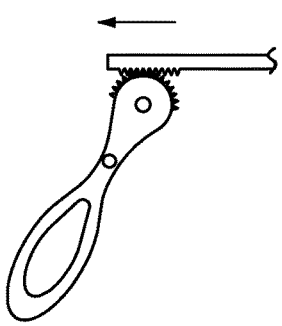
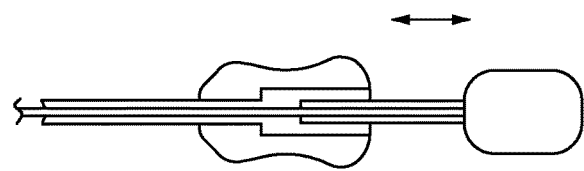
FIG. 9G  FIG. 9H

INFERIOR VENA CAVA FILTER RETRIEVAL DEVICE AND METHOD OF RETRIEVING SAME

This application claims the benefit of and priority to provisional application Ser. No. 62/046,413, filed Sep. 5, 2014, the subject matter of which is also incorporated by reference in its entirety.

FIELD OF THE INVENTION

Inferior vena cava (IVC) filters are small, expanding filters commonly inserted into the inferior vena cava to prevent pulmonary embolism. Fibrosis and skewed deployment can make retrieval using traditional methods difficult or impossible. The present invention is directed to improved devices for retrieving retrievable and non-retrievable IVC filters and to methodologies therefor.

BACKGROUND OF THE INVENTION

Inferior vena cava (IVC) filters are small, expanding filters commonly inserted into the inferior vena cava to prevent pulmonary embolism (see FIG. 1). Retrievable filters may feature a hook on the apex to allow for removal, though non-retrievable filters are sometimes used. Because the risk of embolism is often short-term, removal of the filters is often indicated in hopes of reducing complications such as filter migration or perforation of the vessel wall. However, while placement rates have been steadily increasing, retrieval rates remain low.

The use of inferior vena cava (IVC) filters for therapeutic and prophylactic indications has tremendously increased over the past decade. The majority of the IVC filters placed are retrievable and can be removed when the risk of pulmonary embolism decreases. However, many IVC filters are not retrieved. On the other hand, there are increasing number of case reports of long-term complications of leaving indwelling IVC filters, including IVC thrombosis, filter migration, fracture, and penetration into adjacent structures. These complications require additional endovascular and sometimes open surgeries and are a source of significant morbidity and mortality for the patients and costs on the health care system. As a consequence, the Food and Drug Administration issued an alert to vascular specialists to remove IVC filters from patients in whom protection from pulmonary embolism is no longer needed.

The retrieval of an IVC filter can be a simple and short procedure performed with a snare and a co-axial sheath. Most retrievable filters have a conical design with a hook at the apex that allows snaring the device from above through a jugular access. The vena cava is accessed from the internal jugular vein at the neck, which leads straight past the heart and kidneys to the deployed filter. Using 2D fluoroscopy, the clinician will attempt to snare a roughly 2 mm hook on the apex of the filter and pull it into a sheath for removal. After snaring the hook, a sheath is advanced over the snare to collapse the device and retrieve it. However, this procedure can become very challenging when it is attempted after a long duration from the time the IVC filter was inserted. The struts become incorporated and scarred and are hard to pull out. In some cases, the IVC filter is tilted and the hook cannot be snared. Also, filters can deploy tilted, resulting in the hook resting against the vessel wall. As fibrous tissue builds around this, snare-based retrieval can become difficult or impossible.

Several techniques have been described to allow "difficult" IVC filter retrieval such as the dual-access technique, the balloon-displacement technique, and the sandwich technique among others. The need to "micro-dissect" the fibrotic tissue around the struts is well recognized and has led to the use of unconventional tools by some operators such as rigid bronchoscopy forceps or laser sheath. Even though there is literature reporting success in using those instruments, the safety and effectiveness are not established especially in that they were not designed to retrieve IVC filters.

U.S. Patent Publication Nos. 2002/0045918 and 2014/0031854 illustrate known IVC filter removal devices. However, such devices are only able to move longitudinally relative to the device (e.g. the handle) itself and/or the vessel in which it is positioned as neither describe or suggest any type of articulation (i.e. side to side movement) as disclosed and claimed herein.

SUMMARY AND OBJECTIVES OF THE INVENTION

It is thus an objective of the present invention to overcome the deficiencies of prior art IVC retrieval devices.

Still further it is an objective of the present invention to provide an improved IVC retrieval device that facilitates the removal of an IVC filter that has become lodged in the vessel wall, for example because of the struts or hook thereof having become ensnared in the vessel walls and/or embedded in the fibrotic tissue of the walls.

It is yet another objective of the present invention to provide an improved IVC retrieval device that facilitates the removal of an IVC filter that has otherwise simply become tilted therefore making the hook thereof more difficult to grasp.

Another objective of the present invention to provide an improved IVC retrieval device that facilitates the removal of an IVC filter in which scarring of the struts and penetration into adjacent structures prevent the IVC filter from collapsing.

And it is still a further objective of the present invention to provide an improved IVC retrieval device that facilitates the removal of an IVC filter by dissecting the tissue surrounding the embedded struts of the IVC filter to release the struts from the tissue without excessive penetration into the vessel wall and with a reduction of the risk of perforation.

Yet another objective of the present invention is to provide methodologies and assemblies for carrying out such methodologies that yields fewer complications than achievable with prior art IVC retrieval devices and methodologies using such devices.

Still further, another objective of the present invention is to facilitate the ability of surgeons to perform the improved methodologies as disclosed herein.

Moreover, another objective of the present invention is to provide for an increase in patient satisfaction for all the reasons noted herein.

Still other objects and advantages of the invention will in part be obvious and will in part be apparent from the specification.

The invention accordingly comprises the features of construction, combination of elements, sequence of steps and arrangement of parts which will be exemplified in the construction and methodology hereinafter set forth, and the scope of the invention will be indicated in the claims.

Therefore, while the present invention is generally directed to medical devices for retrieving an inferior vena cava filter from an inferior vena cava, and methodologies using such devices, several preferred embodiments are disclosed therefor.

For example, in a first preferred embodiment, the present invention is directed to a medical device for retrieving an inferior vena cava filter from an inferior vena cava, comprising a handle; a first shaft section coupled to the handle, the first shaft section having a longitudinal axis; a grasping assembly coupled to the first shaft section, wherein the grasping assembly comprises a tube section having a distal end; and a grasper displaceable out of the distal end of the tube section, the grasper for grasping the inferior vena cava filter positioned within the inferior vena cava; a grasper retractor assembly for displacing the grasper out of the tube section and for retracting the grasper into the tube section; and an articulation assembly coupled to the grasping assembly for causing the grasping assembly to move laterally with respect to the longitudinal axis of the first shaft section.

In another preferred embodiment, the present invention is directed to a medical device for retrieving an inferior vena cava filter from an inferior vena cava, comprising a handle; a first shaft section coupled to the handle, the first shaft section having a longitudinal axis; a grasping assembly coupled to the first shaft section, wherein the grasping assembly comprises a tube section having a distal end; and a grasper displaceable out of the distal end of the tube section, the grasper for grasping the inferior vena cava filter positioned within the inferior vena cava; a grasper retractor assembly for displacing the grasper out of the tube section and for retracting the grasper into the tube section; and a sheath configured to advance over the grasper after the grasper has grasped the IVC filter, the sheath having a cutting edge for cutting and/or dissecting tissue in which one or more struts of the IVC filter is embedded.

In yet another preferred embodiment, the present invention is directed to a method of retrieving an inferior vena cava filter from an inferior vena cava utilizing any of the medical devices disclosed herein, wherein the method comprises the steps of advancing the grasping assembly into a region of the inferior vena cava towards the vena cava filter; advancing the grasper out of the distal end of the tube section; articulating the grasping assembly laterally with respect to the longitudinal axis of the first shaft section and into position to grasp the inferior vena cava filter; grasping the inferior vena cava filter; and retracting the grasper into the tube section and retrieving the inferior vena cava filter from the vena cava.

In still another preferred embodiment, the present invention is directed to a method of retrieving an inferior vena cava filter from an inferior vena cava utilizing any of the medical devices disclosed herein, wherein the method comprises the steps of advancing a gasping assembly into a region of the inferior vena cava towards the vena cava filter; advancing a grasper out of the distal end of a tube section; grasping the inferior vena cava filter; cutting and/or dissecting tissue in which one or more struts of the IVC filter is embedded in the inferior vena cava vessel prior to the step of retracting the IVC filter into the tube section and retrieving the inferior vena cava filter from the vena cava. In a specific embodiment, the method may also comprise the steps of rotating the sheath to cut tissue of the inferior vena cava adhering to one or more struts of the IVC filter that is being retrieved and retracting the grasper into the tube section before retrieving the inferior vena cava filter from the vena cava. In still another specific embodiment, the method may also comprise the steps of articulating the grasping assembly laterally with respect to the longitudinal axis of a handle and/or a first shaft section and into a position to grasp the inferior vena cava filter that may be, for example, in a tilted position in the inferior vena cava, and grasping the inferior vena cava filter.

In still another preferred embodiment, a medical device for retrieving an inferior vena cava filter from an inferior vena cava comprises a handle having a distal end, wherein a longitudinal axis is defined thereby; a grasping assembly coupled to the handle, wherein the grasping assembly comprises a grasper for grasping the inferior vena cava filter positioned within the inferior vena cava; and an articulation assembly coupled to the grasping assembly for causing the grasping assembly to move laterally with respect to the longitudinal axis of the handle.

And in yet another preferred embodiment, a method of retrieving an inferior vena cava filter from an inferior vena cava utilizing a medical device as disclosed herein comprises the steps of advancing the grasping assembly into a region of the inferior vena cava towards the vena cava filter; articulating the grasping assembly laterally with respect to the longitudinal axis of the handle and into a position to grasp the inferior vena cava filter; and grasping the inferior vena cava filter.

And still in yet another preferred embodiment, a method of retrieving an inferior vena cava filter from an inferior vena cava utilizing a medical device as disclosed herein comprises the steps of advancing the grasping assembly into a region of the inferior vena cava towards the vena cava filter; grasping the inferior vena cava filter; and cutting and/or dissecting tissue in which one or more struts of the IVC filter is embedded in the inferior vena cava vessel prior to the step of retrieving the inferior vena cava filter from the vena cava.

Reference herein is made to an articulation assembly that is able to cause the grasping assembly to move in a direction other than only along a longitudinal axis, i.e. from "side to side" or "laterally", all of which means in a direction other than along the longitudinal axis of a handle or a shaft section of the medical device as will be discussed further below. What this is intended to mean is that the grasping assembly can move laterally i.e. from side-to-side (and/or "in an out" relative to this page, for example) within and relative to the vessel in which the IVC filter is lodged without being required to simply tilt the device 10. Only being able to move longitudinally would mean simply only in the same direction as the longitudinal axis of the shaft section (i.e. section 50) or handle 40 of the device 10 or vessel as depicted in the prior art references noted above.

In addition, reference to "grasping" or "grasp" or the like is intended and therefore should be interpreted to mean either grabbing the hook or loop or the like of the IVC filter and/or having the arms/jaws of the grasper simply getting entangled in the struts of the IVC filter.

BRIEF DESCRIPTION OF THE DRAWINGS

For a fuller understanding of the invention, reference is had to the following description taken in connection with the accompanying drawings, in which:

FIGS. 6A, 6B, 6C, 6D and 6E are illustrations of a sequence of preferred steps in carrying out preferred embodiments of methodologies using any one of the medical devices that may be constructed as set forth herein. Specifically, FIG. 6A is a view representative of any of the devices 10 as it is moving into position in the vessel to retrieve a tilted and/or embedded IVC filter; FIG. 6B is a view representative of any of the devices 10 showing how the grasping assembly can move from side to side, relative to a centerline $C_1$, the centerline representing the centerline of the vessel or the centerline of a shaft portion 50 as further disclosed herein; FIG. 6C is a view representative of any of the devices 10 as the grasper 25 is extended out of the tube section 12 for retrieval of the tilted and/or embedded IVC filter; FIG. 6D is a view representative of any of the devices 10 again showing how the grasper 25 can move off of the centerline and from side to side (i.e. both to the right and to the left (and in/or out of the page)) to retrieve a tilted and/or embedded IVC filter; and FIG. 6E is a view representative of any of the devices 10 as the grasper 25 is being retracted into the tube section 12 representative of showing that the tilted and/or embedded IVC filter has now been grasped, with the figures generally further illustrating a sheath 150 constructed in accordance with the present invention, with the sheath having a cutting edge for cutting and/or dissecting tissue in which one or more struts of the IVC filter may be embedded, with FIG. 6E showing how the sheath has been moved down into position over the grasping assembly and cutting the tissue at point P, further illustrating how the sheath may be rotated so as to cut and/or tear additional tissue as disclosed herein;

FIGS. 8A-8J illustrate additional configurations and constructions of alternative embodiments and features of the present invention, wherein FIG. 8A illustrates the use of a mechanical joint that may be used as part of the articulation assembly; FIG. 8B illustrates the use of a compliant tube that may be used as tube section 60; FIG. 8C illustrates the use of capture rings to anchor and/or constrain the tendons as disclosed herein; FIG. 8D illustrates the use of a "cut tube" that can used as the flexible tube section as disclosed herein; FIG. 8E illustrates the use of a "stacked" sections resembling a vertebrae that could be used as tube section 60; FIG. 8F illustrates the use of a "compliant beam" structure that could be used as tube section 60; FIG. 8G illustrates the use of a thumb lever with a different attachment arrangement of the tendons for pulling on the grasping assembly as disclosed herein; FIG. 8H illustrates a ball joint configuration that may be used as part of the articulation assembly; FIG. 8I illustrates a "trigger" assembly for pulling on the tendon(s) as disclosed herein and FIG. 8J illustrates the use of a "paddle" lever for pulling on the tendon(s) as disclosed herein; and FIGS. 9A-9H illustrate yet additional configurations and constructions of alternative embodiments and features in connection with the grasping assembly of the present invention, wherein FIG. 9A illustrates the use of a linkage to open and close the grasper; FIG. 9B illustrates the use of a slot/peg arrangement for opening and closing the grasper; FIG. 9C illustrates the use of a retractable springs used to open and close the grasper; FIG. 9D illustrates the use of a gears for opening and closing the grasper; FIG. 9E illustrates the use of a different lever assembly for acting upon the tendon(s); and FIGS. 9F, 9G and 9H illustrate respectively alternative linkage, gearing and direct push/pull arrangements for operating the grasping assembly as disclosed herein.

Figure 1:
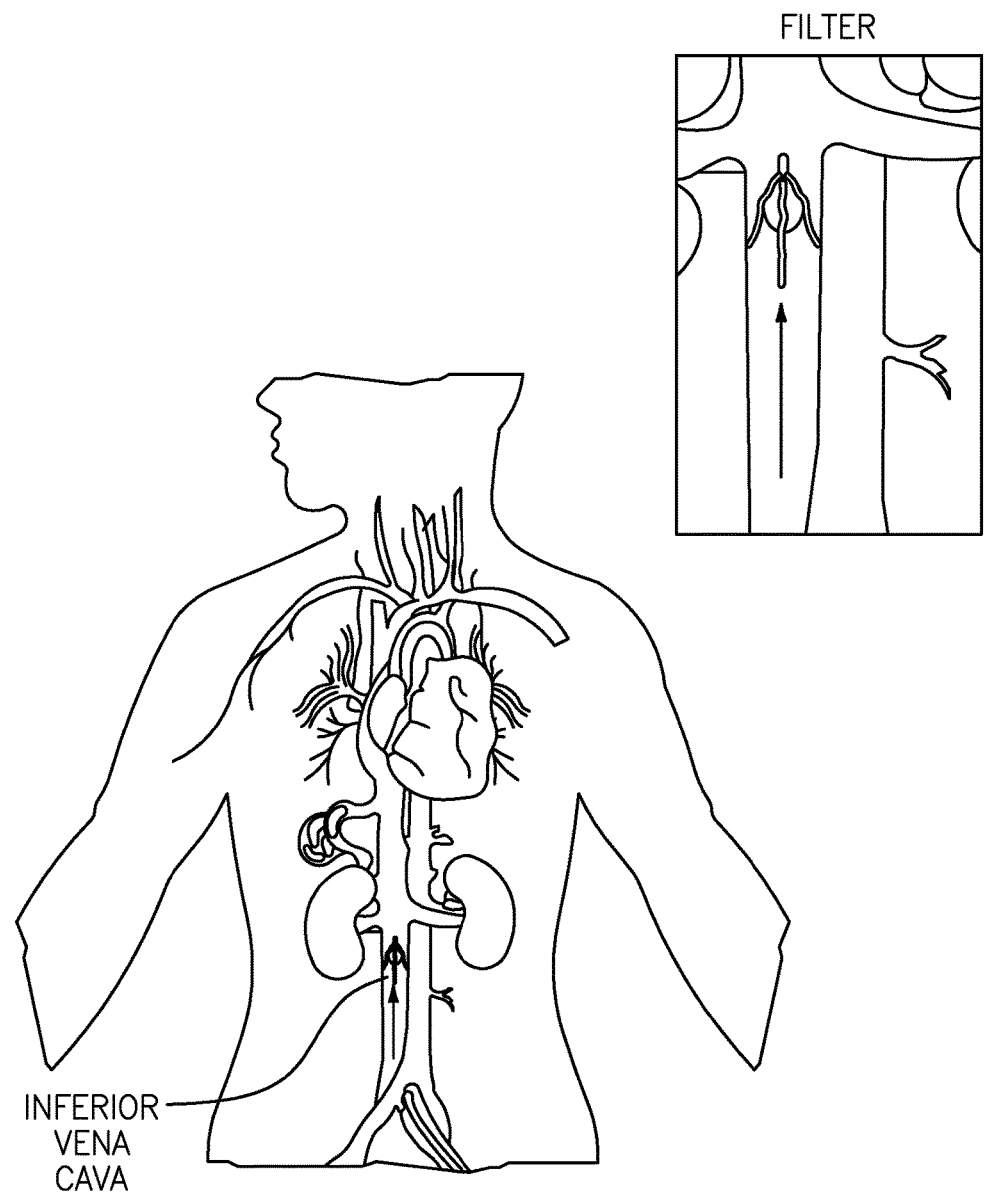
FIG. 1 is a simple diagram of a venous system and exemplary placement of an IVC filter.

In addition, it will be recognized after a review of the current specification, that the figures are not all in scale among themselves or therebetween. However, if each feature was illustrated to scale within each figure, there would be a need for larger paper or smaller images. Therefore, for the convenience of the reader, the scale has been adjusted for ease of understanding. Specific dimensions for components are provided where appropriate and/or helpful. Where not provided, it is readily assumed that those skilled in the art will understand the features and relative sizes disclosed herein.

As will be explained further below, simply tilting the entire device (e.g. handle) so as to move the grasper laterally off of the centerline and from side to side is not what is intended by the present invention, as will be explained in greater detail below.

Lastly, like numbers to identify like parts and features will be used among the various figures, but not all features will be specifically identified in each illustration.

DETAILED DESCRIPTION OF THE PREFERRED EMBODIMENTS

The present invention and the preferred embodiments disclosed herein are directed to improved medical devices for removing retrievable IVC filters, although the present invention is also applicable to the retrieval of non-retrievable filters.

Generally speaking, the preferred embodiments of the present invention are directed to IVC filter retrieval devices that are applicable to the removal of challenging IVC filters. Components of the present invention preferably comprises a roticulating IVC filter retrieval device and/or a dissecting sheath 150. The IVC filter retrieval device preferably has a rigid shaft with an ergonomic handle. The jaws of the grasper are approximately 1.5 cm long, and feature interlocking teeth at the front of the jaw to aid grasping. Proximal of the jaw, the tool can actively articulate in at least one plane. The sheath and the device 10 can also be rotated 360 degrees to give an additional degree of freedom. The sheath is preferably made of plastic and includes a dilator, a side-port to allow flushing and a valve to prevent bleeding when instruments are passed. The outer diameter is preferably 12 French. The tip of the sheath is unique and may have a sharp, cutting indentations that allow the operator to "dissect" or shear tissue by rotating the sheath. The tip of the sheath may be smooth when introduced over the dilator and does not shear the vessel at the point of entry. After removal of the dilator, the sharp edges can be exposed and can engage fibrotic tissue and shear it when the sheath is rotated.

Two factors that may prevent or make IVC filter retrieval difficult are tilt and scarring. First, tilting of the IVC filter makes snaring of the hook more difficult. In some cases, the hook of the tilted filter is in contact with the IVC wall and is embedded in fibrotic tissue. The snare can no longer engage the hook of the IVC filter. The IVC filter retrieval device can manipulate the IVC filter from the hook or the top of the cone that is accessible and pull the IVC filter back into a central position and away from the wall of the IVC. After repositioning the IVC filter, the hook can be secured by the IVC filter retrieval device before advancing the sheath to collapse the filter. The roticulating elbow (i.e. section 60 as disclosed below) of the IVC filter retrieval device gives unique freedom of motion and orientation to allow the operator to recapture the IVC filter rapidly from different parts without the restriction of access to the hook. Furthermore, the ability to secure the IVC filter with a grasper as constructed herein allows the retrieval of pet IVC filters that do not have hooks if they become a source of complication.

Second, scarring of the struts and penetration into adjacent structures prevent the filter from collapsing under pressure from the sheath. The operator exerts traction on the IVC filter retrieval device 10 to collapse the filter into the sheath 150. The cutting side edges of the sheath get in contact with tissue embedding the struts. By rotating the sheath 150, the operator can dissect the tissue in a smooth, controlled fashion to release the tissue from the struts but without excessive penetration into the wall and risk of perforation.

In a preferred embodiment, the device consists of a 12 Fr sheath, with an annular dissecting tip, into which is inserted a grasping tool. In this preferred embodiment, the IVC filter retrieval device preferably comprises a grasper, an articulating section, a long tubular body, and an ergonomic handle that allows control of the grasper and articulation. The grasper features interlocking frontal teeth that act as a hook around the filter to prevent slipping. The articulating section allows deflection from the centerline in at least one plane to allow the grasper access to all parts of the vessel cross-section. The handle may allow for one-handed operation and control of the grasper and articulated section.

The articulation and grasper geometry allow access to and manipulation of a filter in any orientation, regardless of access to the standard retrieval hook. In cases where the hook is buried in tissue or a non-retrievable filter is used, retrieval using a snare is impossible, but the disclosed device can secure a grip, dislodge the IVC filter, and retract it into the sheath. The dissecting tip allows cleaner removal of tissue from the filter to free it from the vessel wall.

In a preferred embodiment, the device 10 comprises a claw-like grasper on the distal end of a stiff shaft preferably no larger than 5 mm, an articulating section at the distal tip that allows access to all points of the venous cross-section, and an intuitive user interface that allows control of each component.

Several different preferred designs are contemplated herein, as set forth in FIGS. 2A, 2B, 2C and 2D, which preferably includes a rigid straight shaft with some form of distal articulation. These options match the environmental constraints (e.g. the vena cava is compliant, and can be reached by a straight path from the internal jugular vein) and provide sufficient control to grasp the filter in various configurations.

As indicated above, a preferred embodiment may be 12 Fr (4 mm) in diameter, and a maximum of 16 Fr (5.3 mm). The length is determined by the venous model, but is easily variable without any other design changes. The grasper is preferably linin in diameter, requiring special fabrication.

The preferred embodiments of FIGS. 2A, 2B, 2C and 2D will be discussed together, with the distinctions thereof being noted where applicable and important. Reference will also be made to FIGS. 3A and 3B which correspond in cross-section to the constructions of FIGS. 2A, 2B respectively. In such preferred embodiments, design components may comprise the handle, the articulating assembly and a grasper. The grasper may be made from nitinol or may be machined and heat-treated spring steel, featuring interlocking teeth and a grasping surface. Retraction into an outer tube forces the two anus of the grasper together, allowing manipulation and retaining of the filter.

In a preferred embodiment and as discussed herein, articulation of the grasper may be provided by a spring and tendon system. The coil spring acts as a flexible column; when the tendon is shortened, the same side compresses, steering the grasper in a particular direction. A preferred embodiment may further comprise a spring column, an actuation tendon, and retaining rings 78 for retaining the tendons against the various shaft sections as disclosed below.

If not already appreciated, it will be appreciated below that a pulling on the tendon results in a deflection of the grasping assembly as shown in the figures.

A simple thumb lever may also be provided to retract the articulation tendon(s). This lever may pivot on a 3D printed handle, designed to simulate a two-piece injection molded handle, as illustrated in FIGS. 2A, 2B, 3A and 3B. The grasper may be actuated by an in-line pull-ring, which offers a secure grip for removal of the filter, which can require significant force.

Preferably, the present invention fits into a 12 Fr (4 mm) catheter. A 16 Fr catheter is clinically acceptable, but a smaller device in that same catheter allows for easier sheathing of the filter. This required a grasper and articulation that were under 4 mm in diameter, and could maneuver to any point where a filter might be and accomplish a secure grasp. A third component would preferably be a trigger mechanism to actuate the grasper.

To hold the filter securely in a variety of places, the grasper preferably features two interlocking teeth that prevent the filter wires from slipping out. When retracted, these teeth form a closed loop around the filter legs, making slippage impossible. The grasper itself may be comprised of two compliant beams that are sprung outwards in the open position. By retracting the beams into the metal housing, the two beams are forced together to close the grasp. The present invention offers better strength and manufacturability at a small scale—the grasper is 2 mm wide—than does a typical revolute grasper typically seen on a 5 mm laparoscopic device.

The articulation assembly may comprise tendons around a flexible core, with several capture rings to keep the tendons close to the core. A second, opposing tendon offers bi-directional flexing, and the core is a flexible column of stainless steel fibers. The tendons may be provided as stainless steel wire rope, and the assembly may be affixed to stainless cannula by welding or mechanical means. A preferred articulation assembly comprises two stainless steel tendons, which provide flexion into or out of the page.

Figure 7A:
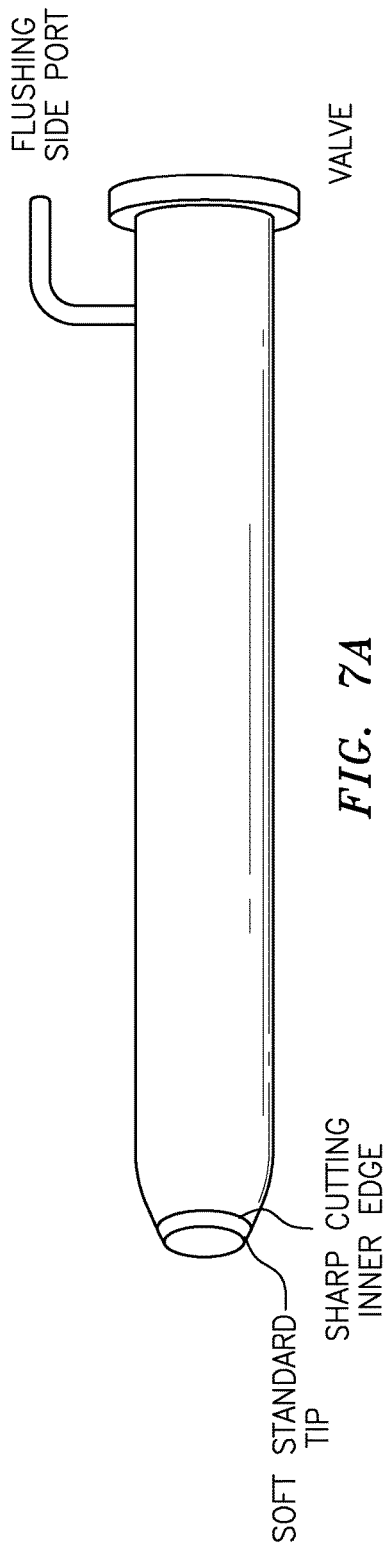
FIGS. 7A, 7B, 7C illustrate the sheath more particularly, with features and advantages in accordance with the present invention.
Figure 7B:
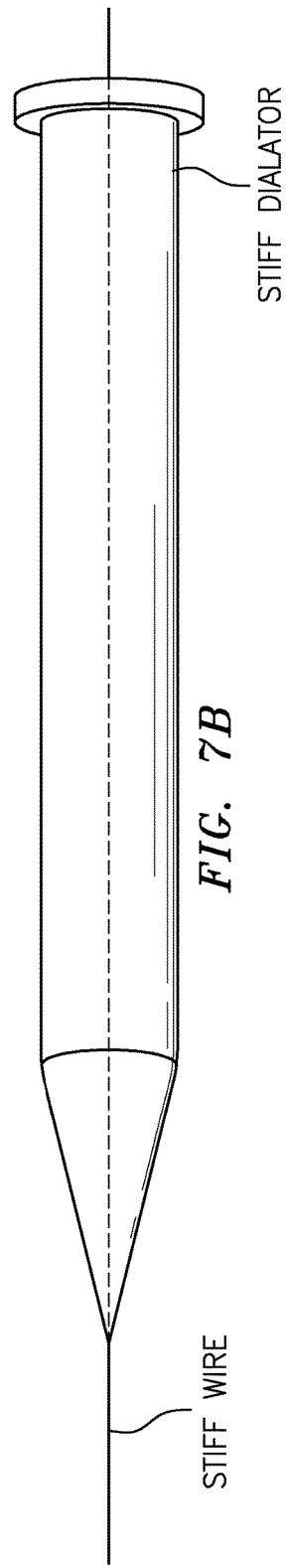
Figure 7C:
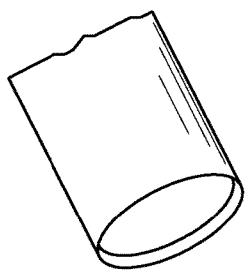
Figure 8A:
Figure 8B:
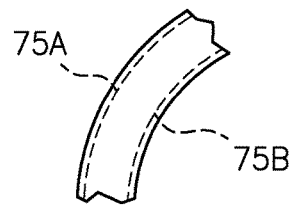
Figure 8C:
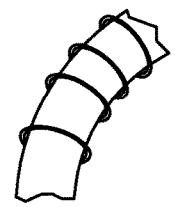
Figure 8D:
Figure 8E:
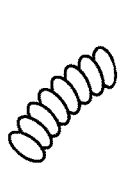
Figure 8F:
Figure 8F:
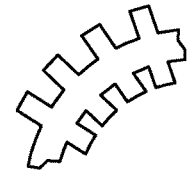
Figure 8G:
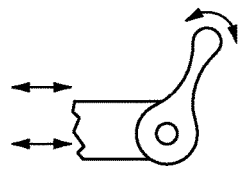
Figure 8H:
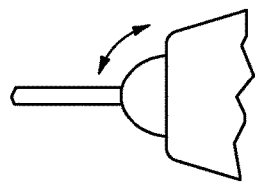
Figure 8I:
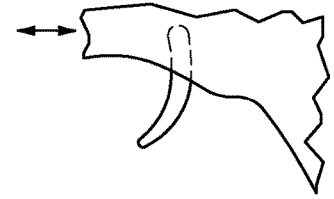
Figure 8J:
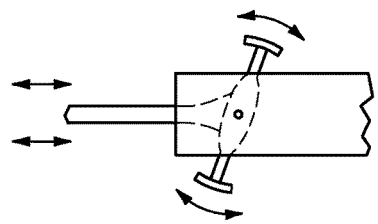

With reference generally to FIGS. 7A, 7B and 7C, dissecting sheath 150 is disclosed, which may be a modification of current sheaths used for endovascular access and therapy. It is preferably 12 French in outer diameter and has a valve and a side port for aspiration and flushing. A unique and advantage characteristic of the dissecting sheath of the present invention is the sharp inner edge that is just proximal to the soft tapered tip (see FIG. 7A). The sheath has a tapered dilator that goes over a stiff standard 0.035" wire to be directed to the inferior vena cava at the level of the renal veins (see FIG. 7B). The sharp cutting inner edge does not protrude beyond the soft tip and does not cause any trauma to the surrounding vessel wall. The inner edge cuts the tissue that is presented to the inner aspect of the sheath only (see FIG. 7C).

The sheath 150 is preferably introduced from the internal jugular vein. The dilator is removed when the sheath is in position in the inferior vena cava. The IVC filter retrieval device (i.e. medical device) 10 is then introduced. After the hook or tip area of the IVC filter is secured in the jaws of the grasper, the sheath is advanced and the IVC filter tends to collapse, drawing the walls of the inferior vena cava radially inward. The fibrosis around the struts of the IVC filter can prevent retrieval of the IVC filter. At this point, the dissecting sheath 150 can be advanced all the way to the ends of the struts that are fixed with fibrotic tissue from the wall of the inferior vena cava. While applying pull back pressure on the grasper, the sheath is advanced forward and at the same time being rotated gently. The rotating motion produces shear forces on the fibrotic tissue surrounding the end of the struts. Only the tissue adherent to the struts will be pulled into the sheath and will get sheared. The surrounding wall of the inferior vena cava is protected by the soft tip and that would minimize risk of transmural injury and perforation. After, dissecting the dense fibrotic tissue on the ends of the struts, the IVC filter may be released from the wall of the IVC and can be retrieved completely into the sheath.

In a desire to make the device operable with one hand, a linkage may be provided to translate trigger motion into movement of the grasper pull-wire. A preferred trigger mechanism and articulation control will be disclosed more fully in connection with the figures below, which illustrate preferred internal mechanisms of the handle. The trigger may be connected to the grasper pull-wire via a linkage that scales the stroke length appropriately. A spring returns the trigger, opening the grasper. Preferably, a thumb lever controls flexion in both directions via the two stainless tendons. The brass cylinder serves as a stop to anchor the tool shaft to the handle shell.

With the foregoing in mind, reference is now made to the figures for a disclosure of specific features of preferred embodiments of the present invention.

Specifically, FIGS. 2A-2D depict a variety of medical device constructions, each generally indicated at 10, in accordance with the present invention, each of which are configured for retrieving an inferior vena cava filter from an inferior vena cava. Devices 10 each comprise a grasping assembly, generally indicated at 20, which may include a grasper cover/tube section 12 having a distal end 12A. Grasping assembly 20 also comprises a grasper 25, which is displaceable out of the distal end 12A of the tube section 12 and configured to grasp and retrieve the inferior vena cava filter positioned within the inferior vena cava. As noted above, grasper 25 preferably comprises two arms 25A, 25B each with preferably (but not necessarily) a respective finger 26A, 26B at each respective distal end thereof. The fingers 26A, 26B assist in grabbing the hook of the IVC filter or otherwise getting "caught" among the struts thereof to facilitate its retrieval into tube section 12. Alternatively, the grasper can be of the "osprey claw" style, e.g. comprising a flat grasping area in addition to overlapping protrusions at the distal end such that when closed the grasper has both two manipulating surfaces and also a "closed loop" aspect.

In a preferred embodiment, grasping assembly 20 comprises a cable 30, preferably made of braided wire or the like, and is coupled at a first end thereof to grasper 25. The coupling of cable 30 to grasper 25 may be by glue, welding, adhesive and/or other adhering ways as would be known to those skilled in the art.

Cable 30 preferably extends all the way back into a handle, generally indicated at 40. Details of the retraction of the grasping assembly 20 will be discussed further below.

Each of the devices 10 also preferably include a rigid, yet hollow rod section, generally indicated at 50, the length of which would be dictated by those skilled in the art for the purpose thereof. An intermediate flexible and hollow tubular "elbow" section, generally indicated at 60, is intermediate rigid rod section 50 and grasper cover/tube section 12. Tube section 60 may be glued, welded or the like at each respective end to tube section 50 and tube section 12.

Each of the devices 10 also includes an articulation assembly, coupled to the grasping assembly 20, for causing the grasping assembly to move in a direction other than along a longitudinal axis of shaft 50. More specifically, the articulation assembly, which includes intermediate flexible and hollow tubular "elbow" section 60, permits the grasping assembly 20 to move in a side-to-side direction, relative to the longitudinal axis of rod section 50 or handle 40. Therefore, in accordance with one embodiment, a longitudinal axis may be defined as the line defined by the connection of a center point at the first end of rod section 50 and a center point at the second end of rod section 50, such as points $P_2$ and $P_3$ defining a longitudinal axis $S_1$ in FIG. 2A or points $P_3$ and $P_4$ defining a longitudinal axis $S_1$ in FIG. 2C, again it being understood that movement of the grasping assembly from side to side is not intended to be met by a device in which the surgeon can simply manipulate the entire device 10 on an angle.

Figure 2A:
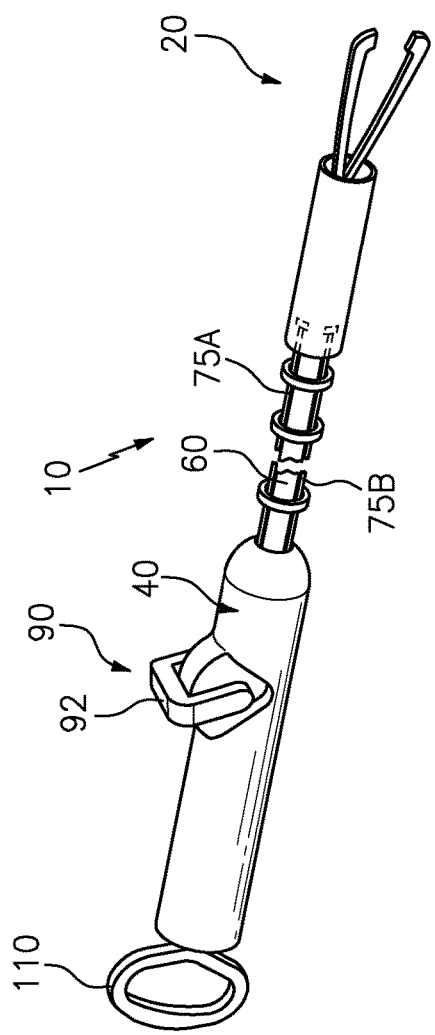
FIGS. 2A, 2B, 2C and 2D show perspective views of different preferred embodiments of medical devices for retrieving IVC filters constructed in accordance with the present invention.
Figure 2B:
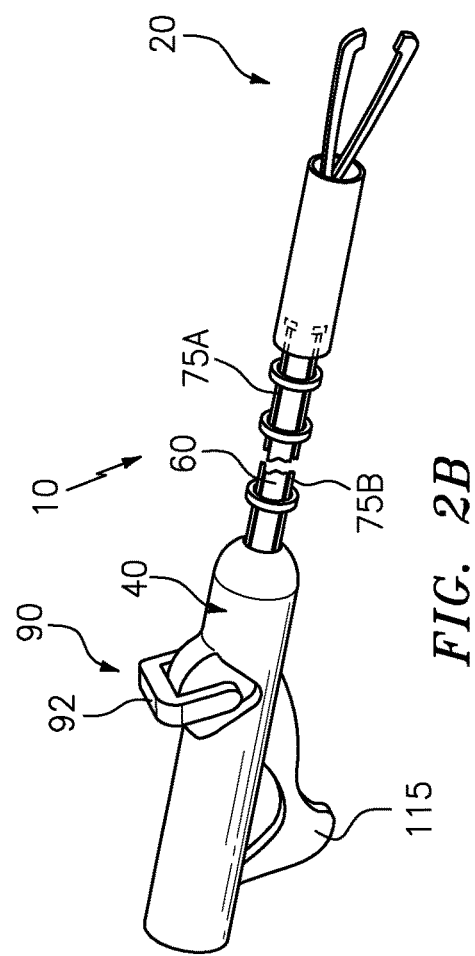
Figure 2C:
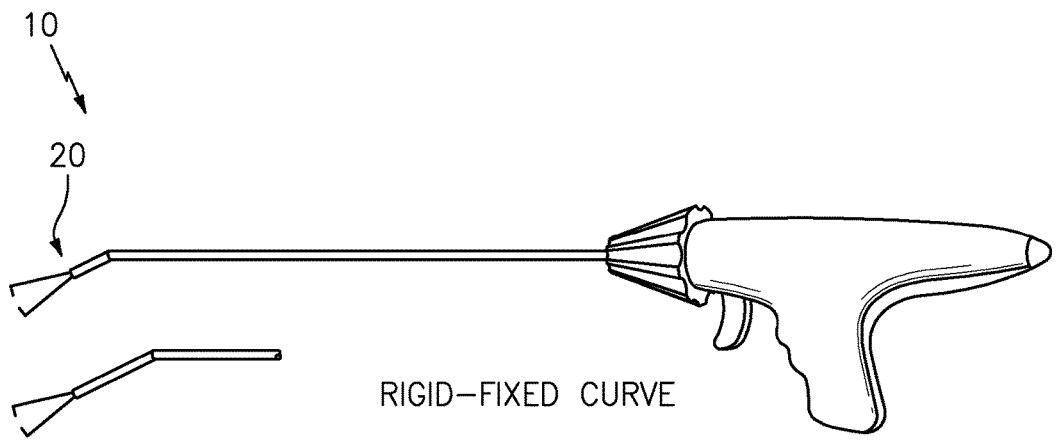
Figure 2D:
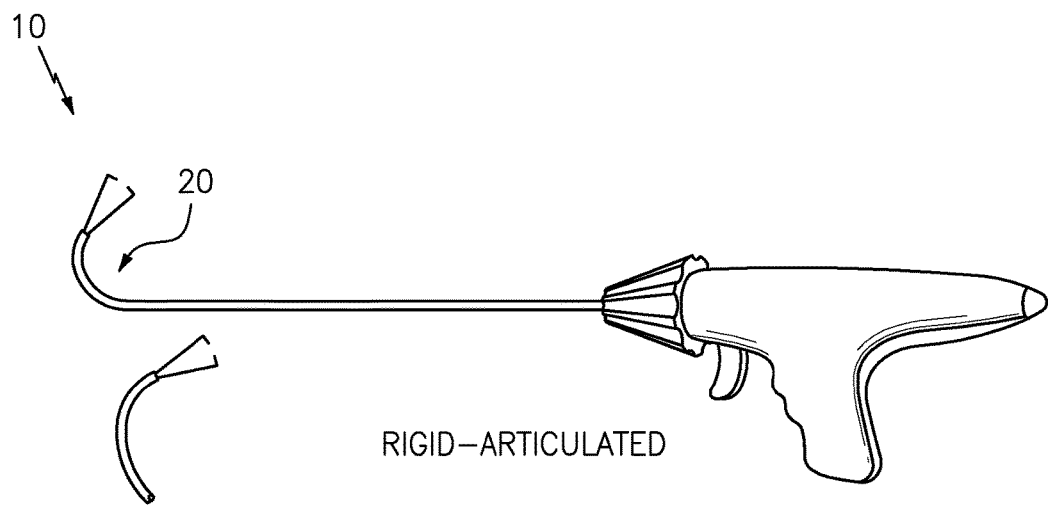
Figure 3A:
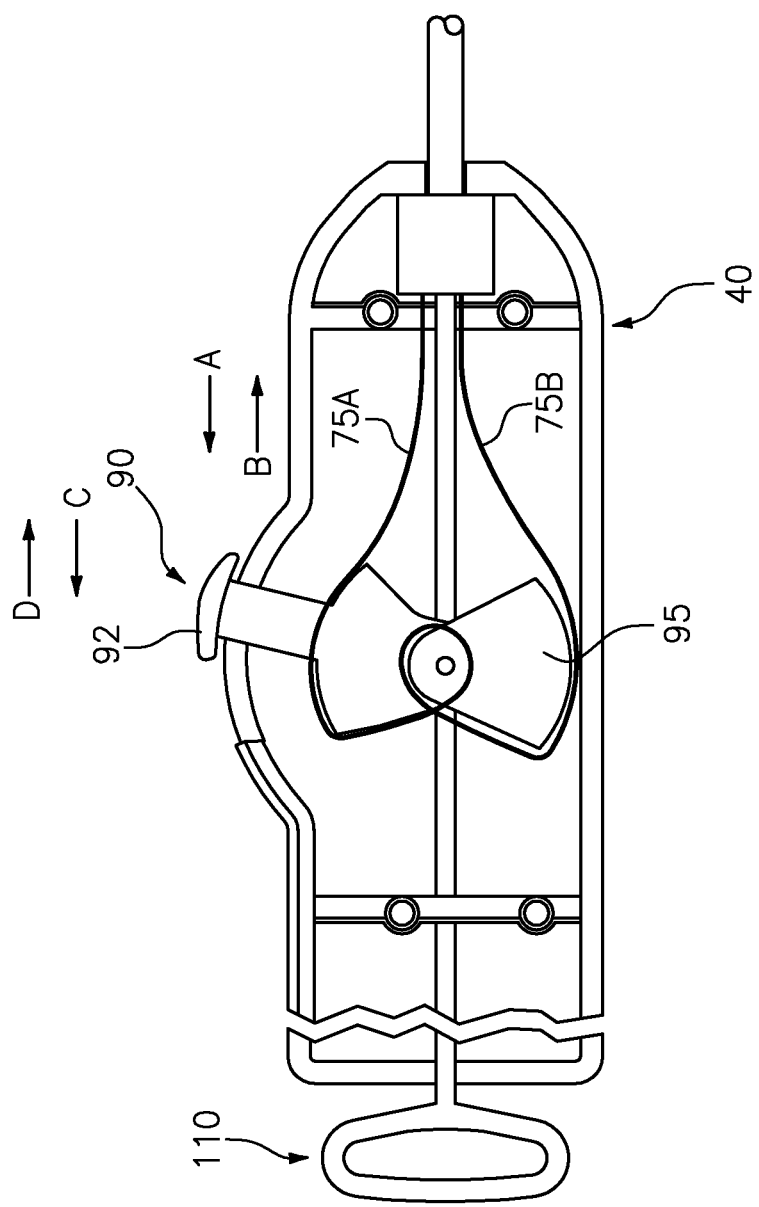
FIGS. 3A and 3B are cross-sectional views of the devices of FIGS. 2A, 2B respectively, illustrating additional features of the present invention.
Figure 3B:
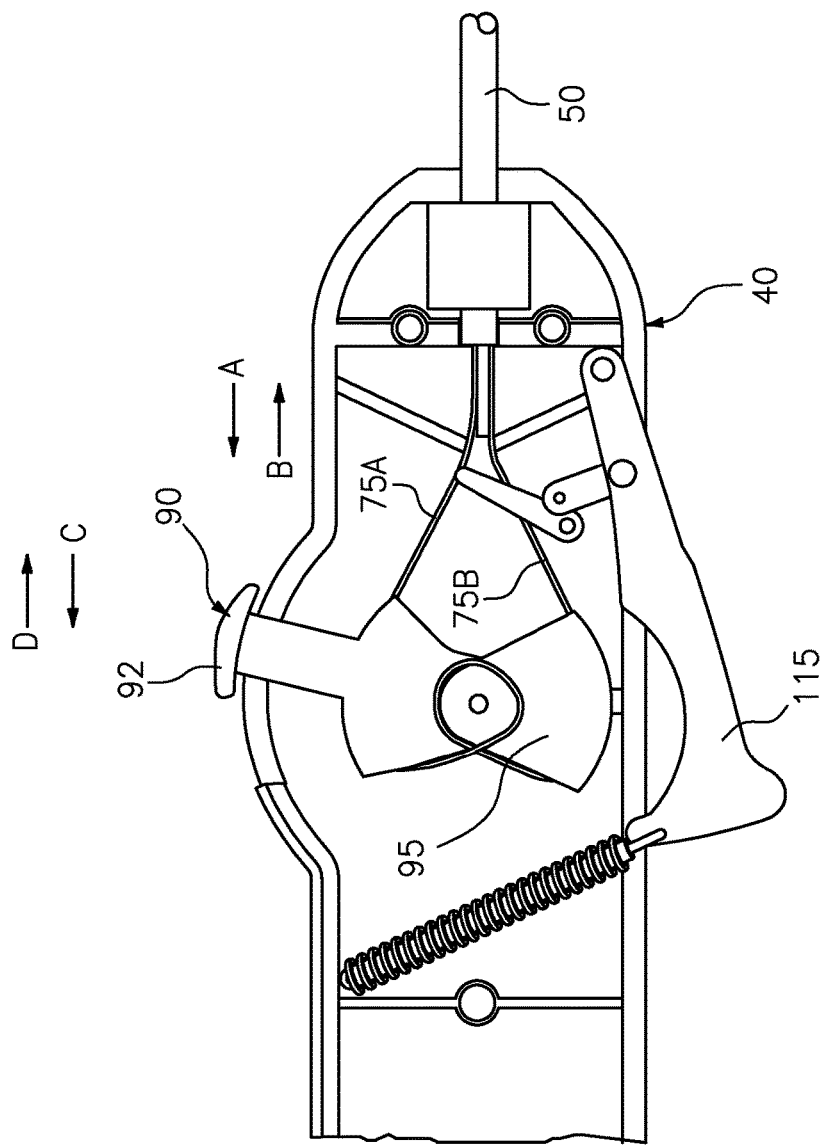
Figure 4:
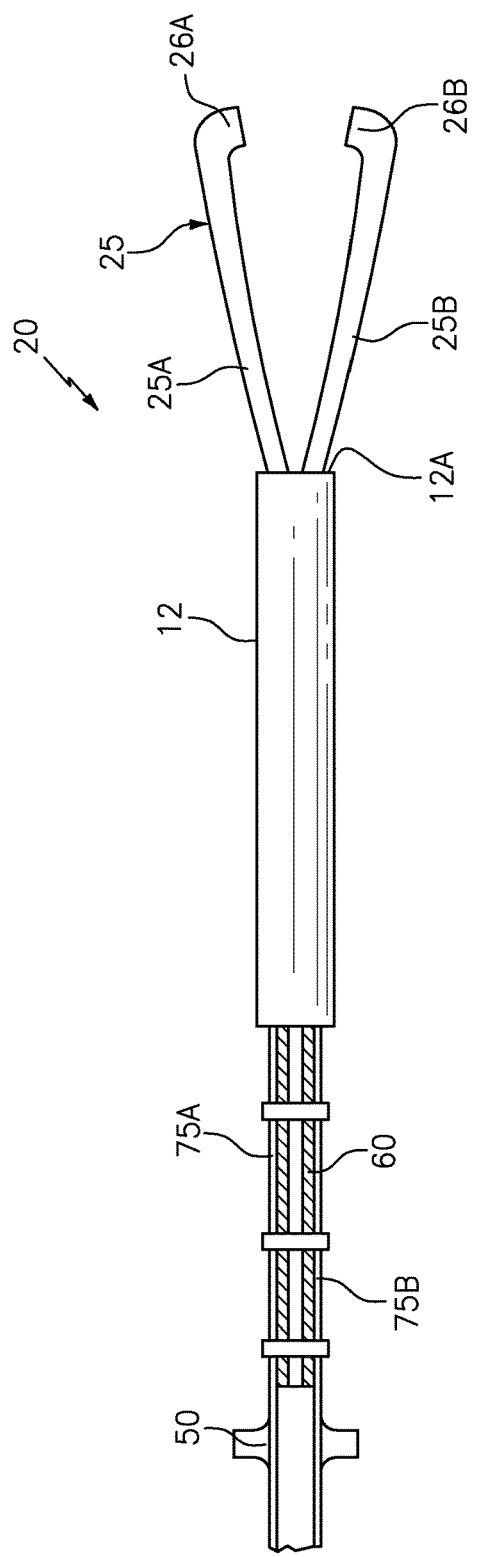
FIG. 4 illustrates yet additional features applicable to all embodiments disclosed herein.

It should also be noted that the longitudinal axis (i.e. axis $H_1$) may be defined simply by two end points on the handle, such as points $P_1$ and $P_2$ as exemplary shown in FIG. 2A. Again, this will permit a patentable distinction between simply moving the entire device 10 from side to side and the inventive feature of having an articulation assembly cause the movement laterally with respect to the longitudinal axis $H_1$ or $S_1$ as illustrated in FIGS. 2A, 2C. It should also be understood that the handle itself may be interpreted to include the shaft section 50 for defining the longitudinal axis. That is, claims herein that recite a handle may itself have a front end that could be interpreted as having a first shaft section for defining the longitudinal axis. In other words, a claim that recites a first shaft section need not have a separate shaft section 50 but rather it could be integral with handle 40, for example, thereby ensuring that the claims are not so limiting.

That is, in accordance with the present invention, the handle 40 of the present invention may remain steady and/or motionless while the grasping assembly 20 and the grasper in particular, is articulating from side to side as will be discussed below.

It is contemplated that shaft 50 may itself be curved, and even in such an embodiment, a longitudinal axis of rod section 50 may be defined for purposes of the claimed invention. For example, and as illustrated in FIG. 2C, points $P_5$ and $P_6$ define a longitudinal axis $S_1$ of section 50.

Figure 5:
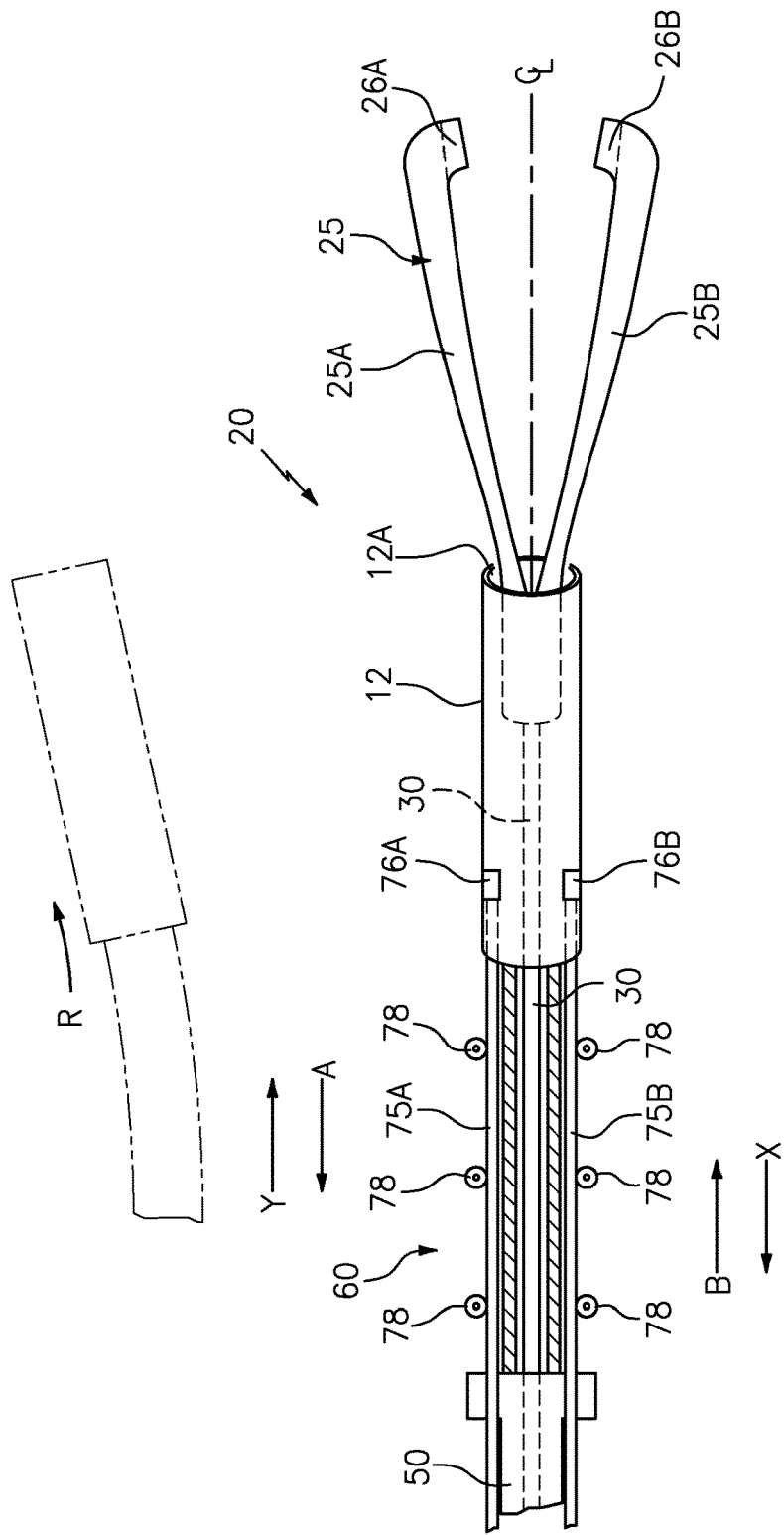
FIG. 5 is a cross-sectional view of FIG. 4.
Figure 6C:
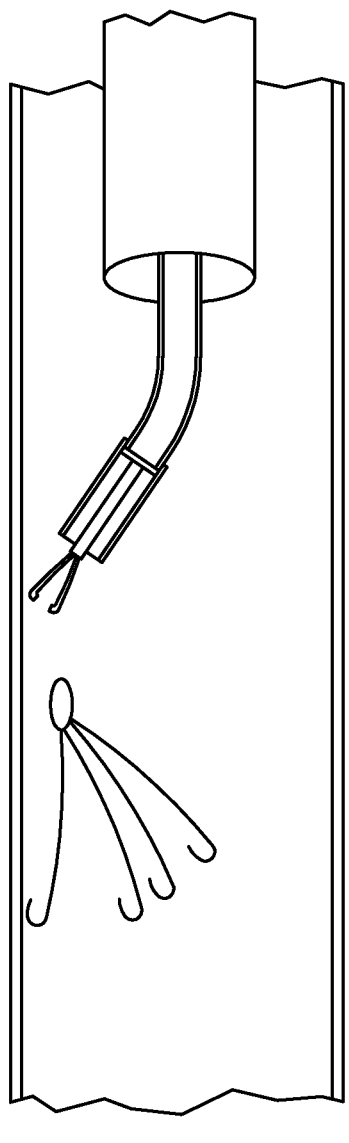
Figure 6D:
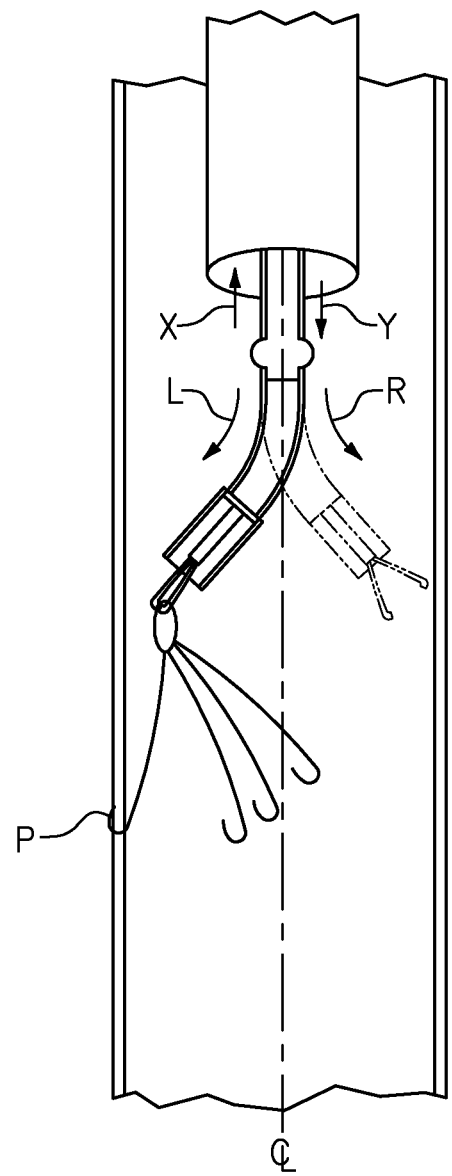

This "side to side," lateral and/or articulating movement is achieved in part by the use of tendons 75A, 75B preferably coupled to the tube section 12, which act, in effect, to "steer" tube section 12 and grasper 25 within the vena cava. As shown in FIG. 5, a distal end of each respective tendon 75A, 75B is directly or indirectly connected or otherwise coupled to preferably the inner or outer sidewalls of tube section 12 at points 76A, 76B, respectively. The connection points are on opposite sides of cable 30. In this way, and as illustrated in FIGS. 5, 6B, 6D, it can be seen that a "pulling" of tendon 75B in the "X" direction (with corresponding tendon 75A being "pushed" in the "Y" direction) will cause grasping assembly 20, and in particular, grasper 25, to deflect or otherwise move from a centerline position (i.e. FIG. 6B) to the left, as viewed in FIG. 6D (with reference to arrow "L"). Similarly, a "pulling" of tendon 75A in the "A" direction with corresponding tendon 75B being "pushed" in the "B" direction (see FIG. 5) will cause grasping assembly 20, and in particular, grasper 25, to deflect or otherwise move from its centerline position to the right, as viewed in FIGS. 5 and 6D (with reference to arrow "R"). Movement to the "right" and/or "left" is intended to be relative to a centerline ($C_1$) of shaft 50, as depicted in FIG. 5.

Reference is thus next made to FIGS. 3A and 3B for additional disclosure of the articulation assembly. That is, all the medical devices 10 disclosed herein preferably comprise a handle 40. FIGS. 2A and 2B illustrate a lever assembly 90, pivotably mounted within handle 40, which includes a lever 92 that can be operated by the surgeon's finger, e.g. a thumb. Lever assembly 90 also includes a rocker or pulley 95 that has tendons 75A and 75B wrapped therearound in a somewhat "FIG. 8" manner such that when lever 92 is moved in the "C" direction (see e.g. FIGS. 3A, 3B), tendon 75A is being "pulled" in the "A" direction and tendon 75B is relaxed. Similarly, when lever 92 is moved in the "D" direction, tendon 75B is being "pulled" in the "X" direction and tendon 75A is relaxed (see FIG. 5). In this way, the tendon being pulled proximally causes the corresponding side of tube section 60 to contract, resulting in the ability of tube section 12 and hence grasper 25 to move from side to side as set forth herein.

FIGS. 3A and 3B illustrate that the tendon(s) can be, if desired, effectively one continuous tendon simply made up of two sections 75A, 75B as disclosed above. Alternatively, tendons 75A, 75B can be separate tendons, but which still preferably utilize the "FIG. 8" rocker or pulley as disclosed herein, or something equivalent to provide for the needed "push" and "pull" functionality of the tendons 75A, 75B. Such is a matter of design choice. Rocker or pulley 95 may have grooves or channels to retain the sections of tendons 75A, 75B therein.

FIGS. 3A and 3B differ in their respective mechanisms for retracting grasper 25 into tube section 12. For example, FIG. 3A utilizes a handle 110 that simply retracts grasper 25 back into tube section 12 by virtue of pulling on cable 30. Alternatively, FIG. 3B illustrates a spring-biased, action trigger 115. That is, a squeezing of the trigger 115 causes, by way of a biased lever action, cable 30 to retract so as to cause grasper 25 to retract into tube section 12. It should be understood that still yet other alternative mechanisms for causing the retraction of grasper 25 into tube section 12 are possible, all of which remain within the scope of the present invention and claims as drafted.

With the above in mind, reference is thus next made to FIGS. 6A-6E for a discussion in connection with a preferred methodology of retrieving an inferior vena cava filter from an inferior vena cava utilizing any one of the medical devices 10 as disclosed herein. As a first step, the tubular section 12 with the grasper 25 therein is advanced in a direction "E" into the inferior vena cava, generally indicated at 1000, and towards the vena cava filter, as would be understood in the art. The procedure may then take varying next steps. For example, the grasper 25 may be advanced out of the distal end of the tubular section 12 (see FIG. 6C). In a procedure where the hook of the vena cava filter is centered within the inferior vena cava and the grasper 25 need not move from side to side but rather the tube section 12 need only extend longitudinally into the inferior vena cava, the arms and fingers of the grasper may simply be advanced until the fingers and/or arms grab the hook of the vena cava filter. As will be noted in the figures, the jaws (i.e. thins 25A, 25B) of grasper 25 are preferably perpendicular positioned to the plane of the tendons, although this is by design choice and not necessity.

Figure 6E:
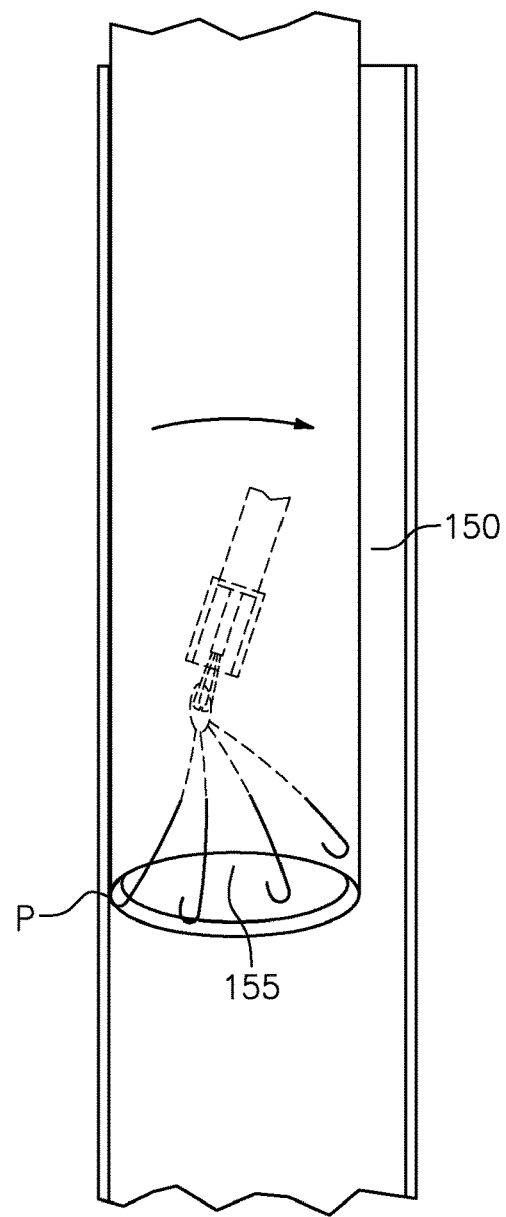

However, where the hook is angled or otherwise positioned nearer the side of the vena cava wall, the present invention provides for the step of articulating the tubular section 12 (e.g. FIGS. 6B, 6D) so that the grasper 25 can grasp the tilted inferior vena cava filter. Specifically, movement of the grasping assembly 20 from side to side, relative to a centerline of the vena cava vessel and/or shaft 50 of the device 10, permits the grasper 25 to grasp the inferior vena cava filter. After grabbing the IVC filter, grasper 25 is then retracted to the tubular section 12 (FIG. 6E). In this way, the grasping assembly 20 retrieves the inferior vena cava filter from the vena cava for removal from the vena cava.

Preferably, the tubular section 12 has an inner diameter large enough to accept the retracted grasper 25 yet small enough to cause the fingers 26A, 26B of grasper 25 to close upon the hook of the vena cava filter, thereby causing the vena cava filter to remain captured in the tubular section 12 and thereafter removed from the vena cava.

Reference is thus also now made again to FIGS. 6A-6E, which illustrates sheath 150 constructed in accordance with the present invention. Sheath 150 has a distal end 155 that has an edge for cutting tissue of the inferior vena cava adhering to one or more struts of the IVC filter that is being retrieved. As alluded to above, after the hook or tip area of the IVC filter is secured in the arms 25A, 25B of the grasper 25, the sheath 150 may be advanced and the IVC filter tends to collapse, drawing the walls of the inferior vena cava radially inward. At this point, the dissecting sheath 150 can be advanced all the way to the ends of the struts (see FIG. 6E) that are fixed with fibrotic tissue from the wall of the inferior vena cava (e.g. region "P"). While applying pull back pressure on the grasper 25, the sheath 150 is advanced forward and at the same time being rotated gently, as illustrated in FIG. 6E. The rotating motion produces shear forces on the fibrotic tissue surrounding the end of the struts. Only the tissue adherent to the struts will be pulled into the sheath and will get sheared. After dissecting the dense fibrotic tissue on the ends of the struts, the IVC filter may be released from the wall of the IVC and can be retrieved completely into the tube section 12.

Therefore, another embodiment of the present invention includes methods of retrieving the inferior vena cava filter from an inferior vena cava utilizing a medical device as disclosed above with and without the aforementioned sheath 150. In such embodiments, the method may comprise the steps of advancing the grasping assembly into a region of the inferior vena cava towards the vena cava filter; advancing the grasper out of the distal end of the tube section; articulating the grasping assembly laterally with respect to the longitudinal axis of the handle and/or the first shaft section and into position to grasp the inferior vena cava filter; grasping the inferior vena cava filter; and retracting the grasper into the tube section and retrieving the inferior vena cava filter from the vena cava. In yet a specific embodiment, with the device comprising a sheath 150 configured to advance over the grasper after the grasper has grasped the IVC filter, the sheath having a cutting edge, the method may comprise the further steps of cutting and/or dissecting tissue in which one or more struts of the IVC filter is embedded in the inferior vena cava vessel prior to the step of retracting the IVC filter fully into the tube section so as to retrieve the inferior vena cava filter from the vena cava. Still further, the method may comprise the steps of rotating the sheath 150 to cut tissue of the inferior vena cava adhering to one or more struts of the IVC filter that is being retrieved.

In yet an alternative embodiment, the method of retrieving an inferior vena cava filter from an inferior vena cava utilizing a medical device as disclosed herein may comprise the steps of advancing the grasping assembly into a region of the inferior vena cava towards the vena cava filter; advancing the grasper out of the distal end of the tube section; grasping the inferior vena cava filter; cutting and/or dissecting tissue in which one or more struts of the IVC filter is embedded in the inferior vena cava vessel prior to the step of retracting the IVC filter fully into the tube section so as to retrieve the inferior vena cava filter from the vena cava and/or optionally rotating the sheath to cut tissue of the inferior vena cava adhering to one or more struts of the IVC filter that is being retrieved. The IVC filter may then be retracted by the grasper into the tube section so as to retrieve the inferior vena cava filter from the vena cava.

Several tests allowed for assessing the functionality of the invention. For example, testing of the device was performed in a dimensionally accurate vena cava model, sized for a 6 ft male.

The four initial tests conducted are shown in Table 1 below illustrate validation of the present invention. A clear PVC tube (1" ID, Shore A67 hardness) was used as a test model, back-lit and viewed with a single camera to collapse the image to 2 dimensions and simulate fluoroscopy. Unimpeded binocular vision offers a false advantage in retrieving these filters, so a testing set up was built to simulate fluoroscopy. Light passes through a diffuser into a tent, where a digital camera outputs a live stream of the vena cava model. To simulate fibrotic tissue build up, hot-melt adhesive secured the filter to the vessel wall.

TABLE 1

| Test | Description | Outcome |
| --- | --- | --- |
| Range of motion | Can the grasper reach each part of a 1" ID tube and grab a filter from each of these positions? | Yes, although advantages of rotational control of the grasper itself should be considered further. |
| On-axis filter | Can the device remove a filter in ideal axial orientation? | Yes; in this case the snare may offer advantages of speed and familiarity |
| Skewed filter | Can the device remove a filter if the hook is against the vessel wall, with the opening obscured? | Yes; this validates this device's advantage - this retrieval would be impossible with a snare |
| Stuck filter | Can the device remove a filter that has been fixed with an adhesive to simulate fibrosis? | Yes. |

The present invention was able to consistently capture and retrieve filters from the venous model in any orientation in under two (2) minutes, comparable to snare retrieval procedures known in the art. More importantly, the configurations of the filter did not affect retrieval time dramatically, indicating that the present invention has concrete advantages over several other known methods in difficult retrieval scenarios. These initial tests demonstrate preferred improvements and benefits over the state of the art retrieval devices.

As can thus be seen above, the present invention provides meaningful and significant improvements over known IVC filter retrieval devices, which would otherwise be difficult or impossible to retrieve. For example, the present invention provides better manipulation and precision of access and grasping than provided by known IVC filter retrieval devices. As mentioned prior, some IVC filters become tilted and sometimes embedded in the IVC wall and make snaring impossible. Therefore, an IVC filter retrieval device such as those embodiments disclosed herein provide attractive alternatives that allows placing a steady grip on the filter to manipulate it and retrieve it. Significantly, the present invention provides IVC filters that can be made of suitable size that have reticulating ability and built to transmit sufficient force, benefits that are lacking in the art today.

For example, the dissecting sheath of the present invention is a new concept that has not been used before. Having a sheath that allows access to the target but also can help in shearing, dissecting action with rotation has never been described in the prior art, to the knowledge of the inventors.

The medical device 10 of the present invention (e.g. IVC filter retrieval device and dissecting sheath) will make IVC filter retrieval technically easier. It will allow significantly reduced procedure time, especially for challenging IVC filters that have tilt or that have been in position for a long time. The present invention would be used for routine IVC filter retrieval as it has clear advantages over the snares that are currently available.

The present invention can also be used to retrieve certain non-retrievable filters and is advantageous in connection with such retrievals for the reasons noted herein.

Moreover, while the preferred embodiments and the claims are disclosed in a sequence as set forth herein, the claims are not limited thereby unless specifically recited as such. That is, the steps of the claims may be performed in a different order unless explicitly recited to be required to be performed in a specific order.

In addition to the figures referenced above, FIGS. 8A-8J and 9A-9H illustrate additional configurations and constructions of alternative embodiments and features of the present invention as set forth above. Additional alternatives and modifications to the present invention are also available and should also be understood by those skilled in the art and are within the scope of the invention.

Therefore, in even another preferred embodiment, the present invention is directed to a medical device for retrieving an inferior vena cava filter from an inferior vena cava comprises a handle having a distal end, wherein a longitudinal axis is defined thereby; a grasping assembly coupled to the handle, wherein the grasping assembly comprises a grasper for grasping the inferior vena cava filter positioned within the inferior vena cava, and an articulation assembly coupled to the grasping assembly for causing the grasping assembly to move laterally with respect to the longitudinal axis of the handle.

In a specific embodiment, the grasping assembly comprises a grasper having a first arm and a second arm and wherein the first arm and second arm are movable towards each other to grasp the inferior vena cava filter. As shown in the earlier figures, the movement of the arms towards each other is achieved by retracting the grasper 25 into tube 12. However, as illustrated in the figures of FIGS. 9A-9D, tube 12 may be optional if a mechanism (e.g. linkage, slot/pegs, springs and/or gears) is provided for such opening and closure of the arms/jaws of the grasper. For example, such figures illustrate that the first and second arms may be hingedly coupled to each other. Such FIGS. 9A-9D further show alternative grasper closing assemblies (e.g. wires/tendons) for moving the first and second arms towards each other so as to grasp the inferior vena cava filter.

In such alternative embodiments, the articulation assembly will still preferably comprise at least one tendon coupled to the grasping assembly, such that a pulling of the tendon in a first direction causes the grasping assembly to move to one of the right or the left relative to the longitudinal axis of the handle. All the figures, including FIGS. 8G-8J and FIGS. 9E-9H, illustrate various ways of configuring the articulation assembly using one or more tendons to cause the pulling and relaxing of the tendons, which in turn cause the "side to side" (i.e. lateral) movement of the grasping assembly relative to the handle and/or shaft section 50 as disclosed and claimed herein.

In such a specific alternative embodiment, the articulation assembly may comprise a lever, which may be pivotably coupled to the handle, and wherein the tendon has a first end coupled to the lever and a second end coupled to the grasping assembly and wherein a movement e.g. pivoting of the lever in a first direction causes the grasping assembly to move to one of the right or the left relative to the longitudinal axis of the handle. FIGS. 8G-8J and 9E-9H also show various levers and even a "ball-joint" assembly that can be used therefor. Alternatively, the lever configurations shown in the figures of FIGS. 8 and 9 can each also be configured and/or used for retracting the grasper 25, and one such configuration is shown in FIG. 9H.

In yet a specific preferred alternative embodiment, the medical device may further comprise a first shaft section 50 coupled to the handle, wherein a longitudinal axis is also defined by the first shaft section (see FIGS. 2A, 2C); a tube section having a distal end; and wherein the grasper is displaceable out of the distal end of the tube section; and a grasper retractor assembly for displacing the grasper out of the tube section and for retracting the grasper into the tube section. The flexible section 60, which is part of the articulation assembly and advantageously provides the side to side motion of the grasping assembly, and may also take on various constructions as illustrated in FIGS. 8A-8F.

Based thereon, methods of retrieving an inferior vena cava filter from an inferior vena cava utilizing one or more of these medical device constructions can be used, wherein the method comprises the steps of advancing the grasping assembly into a region of the inferior vena cava towards the vena cava filter; articulating the grasping assembly laterally with respect to the handle and/or a first shaft section and into a position to grasp the inferior vena cava filter; and grasping the inferior vena cava filter.

In a specific embodiment, the grasping assembly comprises a grasper having a first arm and a second aim and wherein the first arm and second arm are movable towards each other to grasp the inferior vena cava filter, and wherein the medical device comprises a sheath configured to advance over the grasper after the grasper has grasped the IVC filter, the sheath having a cutting edge, wherein the method comprises the step of cutting and/or dissecting tissue in which one or more struts of the IVC filter is embedded in the inferior vena cava vessel prior to a step of retrieving the inferior vena cava filter from the vena cava. Additionally, the method may comprise the steps of rotating the sheath to cut tissue of the inferior vena cava adhering to one or more struts of the IVC filter that is being retrieved.

In an alternative embodiment, a method of retrieving an inferior vena cava filter from an inferior vena cava utilizing a medical device as disclosed herein comprises the steps of advancing the grasping assembly into a region of the inferior vena cava towards the vena cava filter; grasping the inferior vena cava filter; and cutting and/or dissecting tissue in which one or more struts of the IVC filter is embedded in the inferior vena cava vessel prior to the step of retrieving the inferior vena cava filter from the vena cava. Similarly, rotating the sheath to cut tissue of the inferior vena cava adhering to one or more struts of the IVC filter that is being retrieved prior to retrieving the inferior vena cava filter from the vena cava is also contemplated herein.

It is also to be understood that the following claims are intended to cover all of the generic and specific features of the invention described herein and all statements of the scope of the invention which as a matter of language might fall therebetween.

The invention claimed is:

1. A medical device for retrieving an inferior vena cava filter having a single loop for grasping from an inferior vena cava, comprising:
   a handle;
   a first shaft section coupled to the handle, the first shaft section having a longitudinal axis;
   a grasping assembly coupled to the first shaft section, wherein the grasping assembly comprises:
      a tube section having a distal end; and
      a grasper displaceable out of the distal end of the tube section, the grasper comprising only a first arm and a second arm, wherein the first arm has a finger at the distal end of the first arm and the second arm has a finger at the distal end of the second arm, wherein the first and second fingers are inwardly facing towards each other for grasping the single loop of the inferior vena cava filter positioned within the inferior vena cava;
   a grasper retractor assembly for displacing the grasper out of the tube section and for retracting the grasper into the tube section; and
   an articulation assembly coupled to the grasping assembly for causing the grasping assembly to move laterally with respect to the longitudinal axis of the first shaft section; and
   a sheath configured to advance over the grasper after the grasper has grasped the IVC filter, the sheath having a distal end and a dissecting edge that does not protrude beyond the distal end for dissecting tissue in which one or more struts of the IVC filter is embedded in the inferior vena cava vessel.

2. The medical device as claimed in claim 1, wherein the articulation assembly comprises:
   a flexible section intermediate the first shaft section and the tube section;
   a lever pivotably coupled to the handle;
   at least one tendon coupled to the lever, and wherein the at least one tendon is coupled to the grasping assembly, such that:
      the pivoting of the lever in a first direction causes the flexing of the intermediate flexible section and the grasping assembly so as to move to one of the right or the left relative to the longitudinal axis of the first shaft section.

3. The medical device as claimed in claim 2, wherein the at least one tendon is configured and coupled to the lever such that:
   the pivoting of the lever in a second direction causes the grasping assembly to move to the other of the right or left relative to the longitudinal axis of the first shaft section.

4. The medical device as claimed in claim 3, wherein the articulation assembly comprises:
   a rocker or pulley coupled to the lever, wherein the at least one tendon has a first end and a second end, and wherein an intermediate section of the tendon is wrapped around the rocker or pulley; wherein:
   the pivoting of the lever in a first direction causes the first end of the tendon to be pulled towards the lever and the pivoting of the lever in a second direction causes the second end of the tendon to be pulled towards the lever.

5. The medical device as claimed in claim 3, wherein the articulation assembly comprises:
   a rocker or pulley coupled to the lever, and
   a second tendon;
   wherein a first end of the at least one tendon is connected to the rocker or pulley and a second end of the at least one tendon is coupled to the grasping assembly and wherein a second end of the second tendon is connected to the rocker or pulley and a second end of the second tendon is coupled to the grasping assembly, and wherein:

the pivoting of the lever in a first direction causes the first tendon to be pulled towards the lever and the pivoting of the lever in a second direction causes the second tendon to be pulled towards the lever.

6. The medical device as claimed in claim 1, comprising a cable having a first end coupled to the grasper and a second end coupled to the grasper retractor.

7. The medical device as claimed in claim 1, wherein the grasper retractor assembly comprises a handle that pulls the grasper into the tube section.

8. A medical device for retrieving an inferior vena cava filter having a single loop for grasping from an inferior vena cava, comprising:

a handle;

a first shaft section coupled to the handle, the first shaft section having a longitudinal axis;

a grasping assembly coupled to the first shaft section, wherein the grasping assembly comprises:

a tube section having a distal end; and a grasper displaceable out of the distal end of the tube section, the grasper comprising only a first arm and a second arm, wherein the first arm has a finger at the distal end of the first arm and the second arm with has a finger at the distal end of the second arm, wherein the first and second fingers are inwardly facing towards each other for grasping the single loop of the inferior vena cava filter positioned within the inferior vena cava;

a grasper retractor assembly for displacing the grasper out of the tube section and for retracting the grasper into the tube section; and a sheath configured to advance over the grasper after the grasper has grasped the IVC filter, the sheath having a distal end and a dissecting edge that does not protrude beyond the distal end for dissecting tissue in which one or more struts of the IVC filter is embedded.

9. The medical device as claimed in claim 8, comprising an articulation assembly coupled to the grasping assembly for causing the grasping assembly to move laterally with respect to the longitudinal axis of the first shaft section.

\* \* \* \* \*